(12) United States Patent
Tredwell

(10) Patent No.: US 9,910,172 B2
(45) Date of Patent: *Mar. 6, 2018

(54) TEMPERATURE COMPENSATION FOR THIN FILM TRANSISTORS IN DIGITAL X-RAY DETECTORS

(71) Applicant: Carestream Health, Inc., Rochester, NY (US)

(72) Inventor: Timothy J. Tredwell, Fairport, NY (US)

(73) Assignee: Carestream Health, Inc., Rochester, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/484,165

(22) Filed: Apr. 11, 2017

(65) Prior Publication Data

US 2017/0219725 A1 Aug. 3, 2017

Related U.S. Application Data

(63) Continuation of application No. 14/463,061, filed on Aug. 19, 2014, now Pat. No. 9,651,690.

(60) Provisional application No. 61/868,219, filed on Aug. 21, 2013.

(51) Int. Cl.
*G01T 7/00* (2006.01)
*G01T 1/24* (2006.01)
*A61B 6/00* (2006.01)

(52) U.S. Cl.
CPC ............ *G01T 7/005* (2013.01); *A61B 6/4233* (2013.01); *A61B 6/58* (2013.01); *G01T 1/247* (2013.01)

(58) Field of Classification Search
CPC .............................. A61B 6/585; A61B 6/4233
See application file for complete search history.

(56) References Cited

U.S. PATENT DOCUMENTS

| 9,651,690 B2* | 5/2017 | Tredwell ................. G01T 7/005 |
| 2008/0075349 A1 | 3/2008 | Ritter et al. |
| 2010/0006767 A1 | 1/2010 | Enomoto |

FOREIGN PATENT DOCUMENTS

| EP | 0 223 545 A2 | 5/1987 |
| EP | 0 792 066 A2 | 8/1997 |

OTHER PUBLICATIONS

International Search Report for International application No. PCT/US2014/051783, dated Jan. 2015, 2 Pages.

* cited by examiner

*Primary Examiner* — Hoon Song

(57) ABSTRACT

A digital radiographic detector uses predetermined calibration information corresponding to a first operating temperature of the detector. The calibration data is accessible by the detector to compensate a radiographic image captured by the detector at a second operating temperature different than the first operating temperature. The operating temperature of the detector is monitored at approximately the time at which the radiographic image is captured at the second temperature.

18 Claims, 4 Drawing Sheets

| Temp | Cal. Data1 | Cal. Data2 | Cal. Data3 | ... |
|---|---|---|---|---|
| ... | | | | |
| 20°C | | | | |
| 25°C | | | | |
| 30°C | | | | |
| 35°C | | | | |
| ... | | | | |

*FIG. 4*

TEMPERATURE COMPENSATION FOR THIN FILM TRANSISTORS IN DIGITAL X-RAY DETECTORS

CROSS REFERENCE TO RELATED APPLICATIONS

This application is a continuation of U.S. patent application Ser. No. 14/463,061, filed Aug. 19, 2014, in the name of Timothy J. Tredwell, entitled TEMPERATURE COMPENSATION FOR THIN FILM TRANSISTORS IN DIGITAL X-RAY DETECTORS, which claims the benefit of U.S. Provisional application U.S. Ser. No. 61/868,219, provisionally filed on Aug. 21, 2013, entitled "COMPENSATION FOR TEMPERATURE DEPENDENCE OF TFT CHARACTERISTICS IN DIGITAL X-RAY DETECTORS", in the name of Timothy J. Tredwell, which is hereby incorporated herein by reference in its entirety.

BACKGROUND OF THE INVENTION

The subject matter disclosed herein relates to diagnostic imaging, in particular, to radiographic imaging using a digital radiographic detector.

Stationary radiographic imaging equipment may be employed to capture x-ray images on an x-ray detector. Mobile radiographic imaging equipment, such as on rolling carts, may also include an x-ray source and a digital x-ray detector to capture x-ray images. The x-ray images may be acquired and stored using various technologies such as computed radiography (CR) and digital radiography (DR).

A digital radiography (DR) detector acquires image data from a scintillating medium using an array of individual photosensors, arranged in a row-by-column two dimensional matrix, in which each photosensor provides a single pixel of image data. Each pixel generally includes the photosensor and a switching element that may be formed in a common plane of a non-single crystal substrate, for example, hydrogenated amorphous silicon (a-Si:H), to construct the photodiode (photosensor) and a thin-film transistor (switching element) in each pixel. In one embodiment, a front plane of a digital x-ray detector includes a two dimensional array of photosensitive elements (pixels), and a backplane of the detector, which is electrically connected to the front plane, includes an array of thin-film transistor (TFT) switches each connected to one of the pixels.

However, there is a need for improvements in the consistency and/or quality of radiographic images, particularly when the images are obtained by an x-ray apparatus designed to use an amorphous silicon based DR detector.

SUMMARY OF THE INVENTION

An aspect of the present disclosure provides a method and apparatus to address disadvantages caused by the use of portable (e.g., wireless) digital radiography (DR) detectors used in mobile radiographic imaging equipment. In one embodiment, a method of operating a digital radiographic detector is disclosed wherein numerical calibration data is determined in association with the detector corresponding to a first operating temperature of the detector. The calibration data is stored in an electronic table accessible by the detector, and is configured to compensate a radiographic image captured by the detector at a second operating temperature different than the first operating temperature. The operating temperature of the detector is monitored at approximately the time at which the radiographic image is captured at the second temperature. In accordance with the magnitude of the second temperature, as monitored, the stored table of the calibration data is modified by a common factor, which may either increase or decrease the stored calibration data.

In another embodiment, method to determine gain correction for a digital radiographic detector is disclosed. The detector includes an array of pixels forming rows and columns configured to generate a radiographic image based upon radiation impacting the pixels. A plurality of gate lines and data lines is provided, wherein each one of the gate lines is coupled to a respective row of pixels and each one of the data lines coupled to a respective column of pixels, and each of the pixels comprise a thin-film transistor (TFT) connected to a photosensor. The method comprises determining a gain correction map for the array of pixels at a first prescribed temperature and at a predetermined set of array operating parameters. By measuring the operating temperature, or at least one temperature sensitive parameter, prior to generating the radiographic image, one or more of the array operating parameters is adjusted in accordance with the temperature to achieve a gain at the operating temperature or at the at least one temperature sensitive parameter substantially equal to a gain at the first prescribed temperature.

In another embodiment, a digital radiography detector for an imaging system is disclosed. The digital radiography detector comprises an array of pixels, forming rows and columns, configured to generate signals based upon radiation impacting the detector. A plurality of scan lines are each coupled to a respective row of pixels and each one of the data lines is coupled to a respective column of pixels. A readout circuit selectively couples the rows of pixels to the respective scan lines and columns of pixels to the respective data lines for read out of the signals. A readout time for the array of pixels is adjusted based on a temperature dependent charge transfer time constant $\tau_{RC}$ of a thin-film transistor in each of the pixels which is configured to connect a photosensor of the pixel to a corresponding data line.

These objects are given only by way of illustrative example, and such objects may be exemplary of one or more embodiments of the invention. Other desirable objectives and advantages inherently achieved by the disclosed invention may occur or become apparent to those skilled in the art. The preceding brief description of the invention is intended only to provide a brief overview of subject matter disclosed herein according to one or more illustrative embodiments, and does not serve as a guide to interpreting the claims or to define or limit the scope of the invention. The invention is defined only by the appended claims and their equivalents. This brief description is provided to introduce an illustrative selection of concepts in a simplified form that are further described below in the detailed description. This brief description is not intended to identify required features or essential features of the claimed subject matter, nor is it intended to be used as an aid in determining the scope of the claimed subject matter. The claimed subject matter is not limited to implementations that solve any or all disadvantages noted in this background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 4 shows an exemplary temperature calibration data table usable with the exemplary radiographic imaging system disclosed herein.

DETAILED DESCRIPTION OF THE INVENTION

Figure 1:
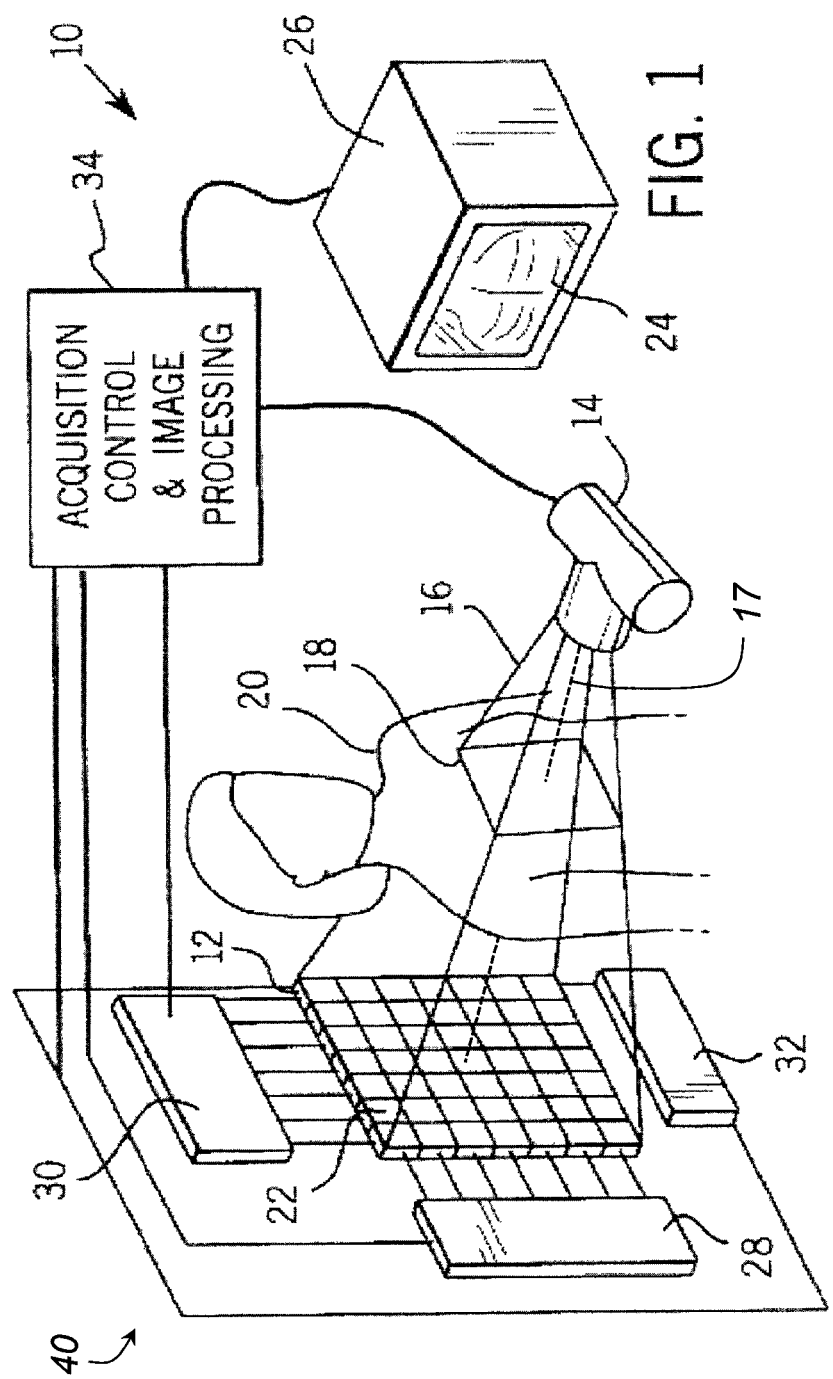
FIG. 1 is a diagram of an exemplary radiographic imaging system.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

FIG. 1 is a perspective view of a digital radiographic (DR) imaging system 10 that includes a generally planar digital radiographic detector 40, an x-ray source 14, and a digital image monitor 26, according to one embodiment. The digital detector 40 may include a two dimensional array 12 of detector cells 22 (photosensors), arranged in electronically identifiable rows and columns. The digital detector 40 may be positioned to receive x-rays 16 passing through a subject 20 during a radiographic exposure, or radiographic pulse emitted by the x-ray source 14. As shown in FIG. 1, the radiographic imaging system 10 may use an x-ray source 14 that emits collimated x-rays 16, e.g. an x-ray beam, selectively aimed at and passing through an area 18 of the subject 20. The x-ray beam 16 may be attenuated by varying degrees along its plurality of rays according to the internal structure of the subject 20, which attenuated rays are detected by the array 12 of photosensitive detector cells 22. The planar digital detector 40 is positioned, as much as possible, in a perpendicular relation to a substantially central ray 17 of the plurality of rays 16 emitted by the x-ray source 14. The array 12 of individual photosensitive cells (pixels) 22 may be identified by their position according to column and row, however, the orientation of the columns and rows is arbitrary and does not limit the scope of any embodiments disclosed herein. For clarity of description, it will be assumed that the rows extend horizontally and the columns extend vertically.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24 that may be digitally decoded and displayed by a digital monitor 26 for viewing by a user. An electronic bias circuit 32 is electrically connected to the detector 12 to provide a bias voltage to each of the photosensitive cells 22.

Each of the bias circuit 32, the scanning circuit 28, and the read-out circuit 30, may communicate with, via a wired or wireless connection, an acquisition control and image processing unit 34 that includes a processor and electronic memory (not shown) to control operations of the detector 40 as described herein below, including circuits 30, 28 and 32, for example, by use of programmed instructions. The acquisition control and image processing unit 34 may also be used to control activation of the x-ray source 14 during a radiographic exposure, controlling an x-ray tube electric current magnitude, and thus the fluence of x-rays in x-ray beam 16, and/or the x-ray tube voltage, and thus the energy level of the x-rays in x-ray beam 16.

The acquisition control and image processing unit 34 may transmit image (pixel) data to the monitor 26, based on the radiographic exposure data received from the array 12 of photosensitive cells 22. Alternatively, acquisition control and image processing unit 34 can process the image data, store raw or processed image data in local or remotely accessible memory or export the image data.

With regard to direct detection, photosensitive cells 22 may each include a sensing element sensitive to x-rays, i.e. it absorbs x-rays and generates an amount of charge carriers in proportion to a magnitude of the absorbed x-ray energy, and a switching element that is selectively activated to read out the charge level of the corresponding sensing element. With regard to indirect detection, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, is disposed over the light sensitive sensing elements to convert incident x-rays to visible light rays.

Examples of sensing elements used in sensing arrays 12 include various types of photoelectric conversion devices (e.g., photosensors) such as photodiodes (P-N or PIN diodes), photo-capacitors (MIS), photo-transistors or photoconductors. Examples of switching elements used for signal read-out include MOS transistors, bipolar transistors and p-n junction components.

Figure 2:
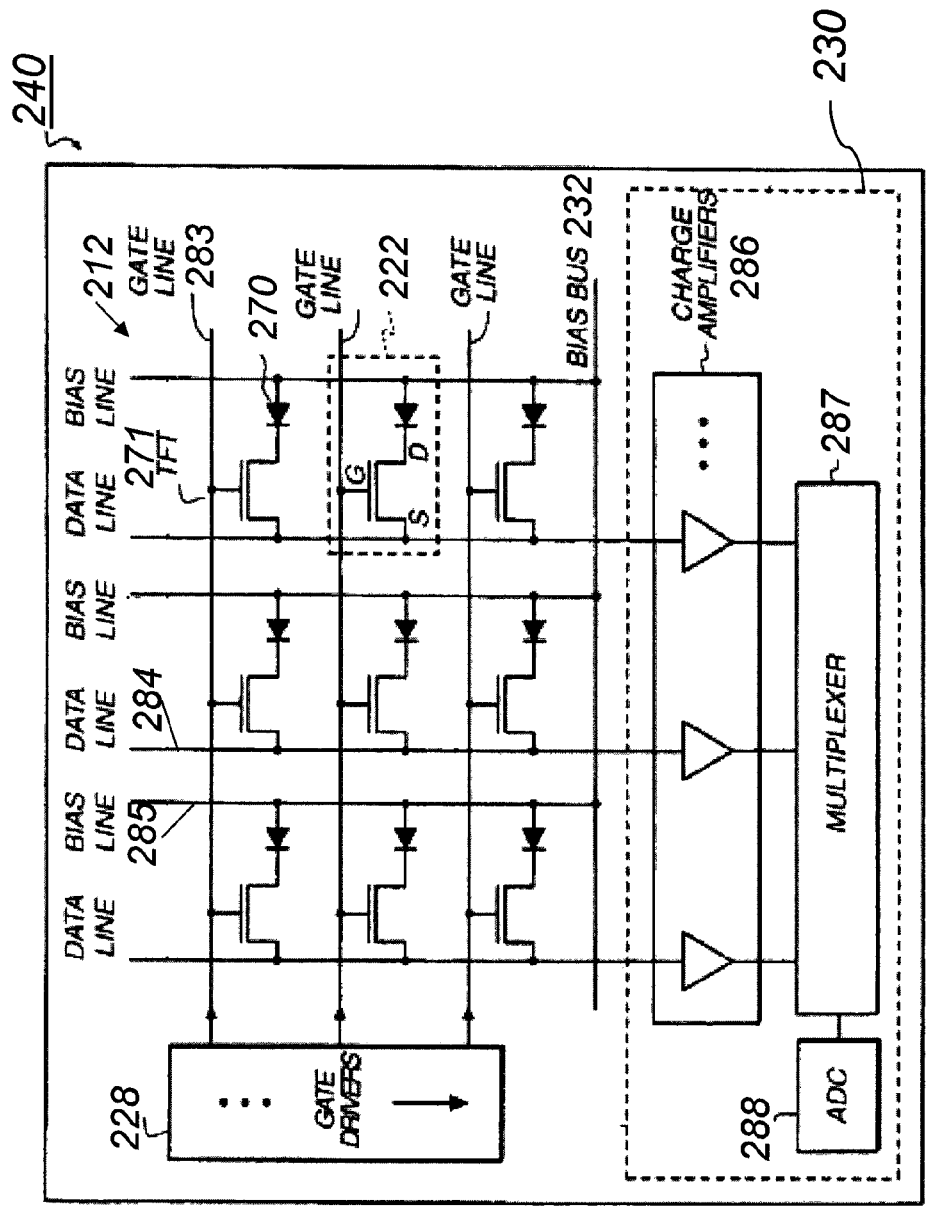
FIG. 2 is a schematic diagram of an imaging array for a radiographic detector.

FIG. 2 is a schematic diagram 240 of a portion of a two-dimensional array 12 for a digital radiographic detector 40. The array of photosensor cells 212 may include a number of a-Si:H n-i-p photodiodes 270 and thin film transistors (TFTs) 271 formed as FETs each having gate (G), source (S), and drain (D) terminals. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital image data at desired rates. In one embodiment, the schematic diagram of FIG. 2 may represent a digital radiographic detector 40 such as a hydrogenated amorphous silicon (a-Si:H) based indirect flat panel imager.

Incident X-ray photons, or x-rays, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 22, 222, which may be equivalently referred to herein as a pixel, may include a photodiode 270 having its anode electrically connected to a bias line 285 and its cathode electrically connected to the drain of TFT 271. The bias reference voltage line 232 can control a bias voltage of the photodiodes 270 at each of the detector cells 22. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency of the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting ("on") state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230. This digital image information may be subsequently processed by image processing system 34 to yield a digital image which may then be stored and immediately displayed on monitor 26, or displayed at a later time by accessing electronic memory containing the stored image. The flat panel imager having an imaging array as described with reference to FIG. 2 is capable of both single-shot (e.g., static, radiographic) and continuous (e.g., fluoroscopic) image acquisition.

Figure 3A:
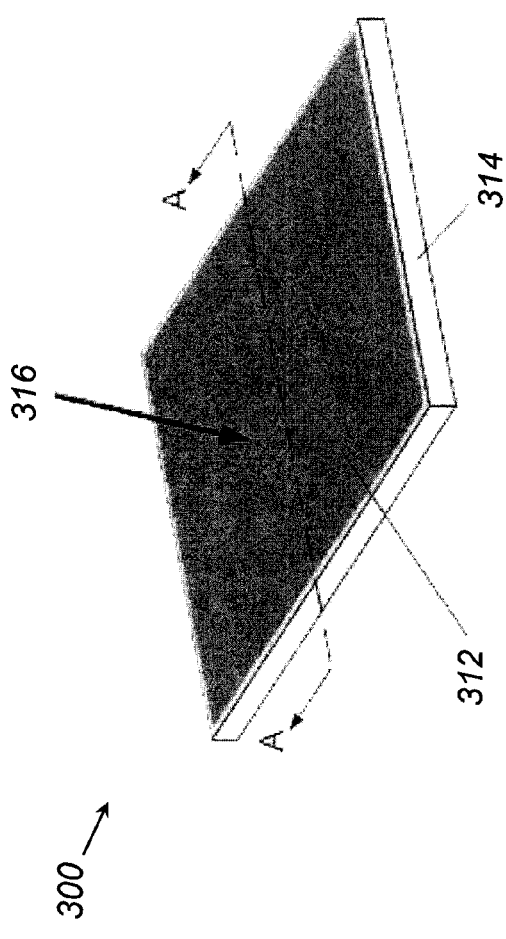
FIG. 3A shows a perspective view of a portable wireless DR detector.
Figure 3B:
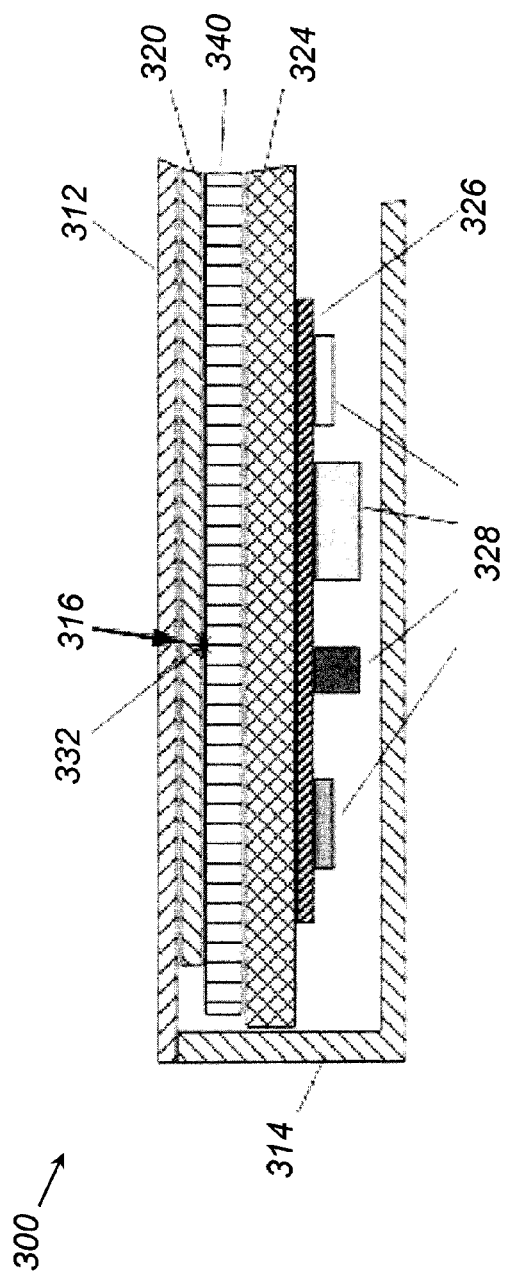
FIG. 3B is a cross-section of a portion of the portable wireless DR detector of FIG. 3A along section line A-A.

FIG. 3A shows a perspective view of a portable wireless DR detector 300 according to one embodiment disclosed herein. FIG. 3B shows a portion of a cross-section view along line A-A of the DR detector 300. As shown in FIGS. 3A-3B, the portable DR detector 300 may include a housing comprising a top cover 312, and enclosure 314, enclosing at least a scintillator 320 and a two-dimensional imaging array 340, as described herein.

In one embodiment, the DR detector 300 housing may include an enclosure 314, having a top cover 312, attached thereto, made of material that passes x-ray flux 316 without significant attenuation. Scintillator 320 may be under (e.g., directly connected to) the top cover 312, and the imaging array 340 may be directly under the scintillator 320. Readout electronics 328 may be co-planar with the imaging array 340, partially below support member 324 or on a flexible connector therebetween. The x-ray flux 316 may pass through the top panel cover 312, impinge upon scintillator 320 where stimulation by high-energy rays, or photons, in the x-ray flux 316 causes the scintillator 320 to emit low energy photons 332 as visible light rays.

The support member 324 can be included to securely and/robustly mount the imager 240 and can further operate as a shock absorber between components therein and the enclosure 314. Device electronics required for proper operation of the detector can be mounted within the enclosure 314 and can include electronic components 328 (e.g., processors, FPGAs, ASICs, chips, etc.) that can be mounted on one or more separate and/or interconnected circuit boards 326.

Exemplary embodiments described herein relate to methods and/or systems of temperature compensation of the TFT transfer characteristics in a digital x-ray detector for the purpose of maintaining calibration over a wide operating temperature range.

In the operation of the DR detector, or digital X-ray detector (DXD), it is advantageous to have the capability of operating over a wide temperature range without requiring pixel-by-pixel calibration or recalibration for each monitored operating temperature. To minimize calibration time and complexity, the pixel-by-pixel gain calibration data for sensitivity to X-ray exposure can be performed at a single temperature (e.g., 25° C.) and stored in a table in electronic memory for later access by the image processing system 34. This gain calibration at a single temperature is typically performed by exposing the detector to a uniform magnitude X-ray exposure and measuring the detector output divided by the X-ray exposure level to give a numerical measure of electrons per incident X-ray on a pixel-by pixel basis, which data may be stored on a pixel-by pixel basis. This single temperature gain calibration data is used to adjust the detector output during detector operation to remove spatial variation in gain. In usage of a DXD, it is desirable for this single temperature gain calibration data to apply over a wider range of operating temperatures, for example, 15° C. to 35° C. However, it is well known that the TFT characteristics can change significantly over even a 20° C. temperature change in the DXD operating temperature. A significant TFT parameter for passive-pixel DXD operation is the channel resistance $R_{TFT}(V_{GS}, -V_T, V_{DS}, T)$ between the source (S) and drain (D) of the TFT where $V_{GS}$ is the voltage between gate (G) and source (S), $V_T$ is the TFT threshold voltage, $V_{DS}$ is the voltage between source and drain and T is the operating temperature. During charge transfer (read out) from the photodiode to the dataline, the TFT gate can be switched to a large positive voltage (such as +25V) in order to turn on the TFT while the source can be held at 0V and the $V_{DS}$ can be <1V. In these conditions, the TFT can be in the linear region of operation and the resistance is independent of $V_{DS}$ to first order. The TFT channel resistance can depend on the inverse of the electron mobility $\mu_e(T)$ as a function of temperature (T). Electron movement in amorphous silicon can be described by a hopping process in which the electron becomes trapped in shallow traps in the amorphous silicon and then is thermally excited out of the trap and transports a short distance under the influence of the electric field between drain (D) and source (S) followed by capture by another trap. Since the hopping process is thermally activated, the mobility has a strong temperature (T) dependence, with higher mobility at higher temperatures. In practice, it is found that the TFT resistance can change by a factor of 2× or more over a 20° C. temperature change in operating temperature of a DXD.

The change in TFT resistance has an effect on the accuracy of gain calibration and the stored gain calibration data may be modified according to the monitored (detected) operating temperature. Charge transfer from the photodiode to the dataline is limited by the charge transfer time constant $\tau_{RC}$, which may be calculated as follows:

$$\tau_{RC} = R_{TFT}(V_{GS}, T) * C_{PD} \quad (1)$$

where $R_{TFT}$ is the TFT channel resistance at gate (G) to source (S) voltage $V_{GS}$ and temperature T, and $C_{PD}$ is the photodiode capacitance. For a typical digital X-ray detector, $R_{TFT}(V_{GS}=25V, T=25°C.)=3$ MΩ and $C_{PD}(V_{PD}=4V, T=25°C.)=3$ pF, for a transfer time constant $\tau_{RC}=9$ μs. In general, the dependence of $R_{TFT}$ on $V_{DS}$ and the dependence of $C_{PD}$ on bias and temperature are small and can be neglected.

During operation, the DR detector is exposed to X-rays with the gates of all of the TFT's in the off-state ($V_{GS}$<0). The detector is then read out by clocking each row of gates to a large positive voltage $V_{GS}$~25V to switch them into a conducting (on) state for a transfer time $T_{TR}$.

For a photodiode exposed to X-rays to create a signal charge $N_0$ electrons, the charge $N_{sig}$ transferred from the photodiode to the dataline during the transfer time is given by:

$$N_{sig} = N_0 * (1 - \exp(-T_{TR}/\tau_{RC})) \quad (2)$$

For a typical DR detector, the transfer time $T_{TR}$ is determined by the desired readout time and is typically 20-50 μs. Both $R_{TFT}$ and $C_{PD}$ are not uniform across the detector area due to process variations in photodiode thickness (which affects $C_{PD}$) and TFT channel length (which affects $R_{TFT}$). This spatial variation in $R_{TFT}$ and $C_{PD}$ can be reduced or removed by determining the detector gain calibration at a single temperature and storing it for later compensation during image capture. However, over a 20° C. temperature range the approximate 2× change in $R_{TFT}(V_{GS}, T)$ will cause the signal charge $N_{sig}$ as read out from the data line to change, resulting in an inability to perform accurate calibration of the DR detector for the operating extremes. This results in the spatial variation to become visible in the X-ray images taken over (e.g., at the extremes) the operating temperature range of a DXD.

Certain exemplary embodiments described herein may provide methods and apparatus to achieve accurate gain calibration over a wide temperature range in a DXD without the need to calibrate and recalibrate at multiple temperatures. Certain exemplary embodiments rely on (i) the dependence of the $R_{TFT}(V_{GS}, T)$ on gate voltage $V_{GS}$ and temperature T or (ii) on monitoring $R_{TFT}$ or a variable related to $R_{TFT}$ in panel operation and adjusting one or more operating points of the panel to achieve a target value of $T_{TR}$ and/or $\tau_{RC}$. In certain exemplary embodiments disclosed herein, the temperature of the DR detector (e.g., or at least one temperature sensitive parameter such as TFT resistance or image lag) during detector readout can be monitored in the x-ray detector cassette and can be used by software in a detector micro-controller in the detector cassette or in the image processor in the detector console 34 to adjust, or modify, settings for detector operation. In several method embodiments described below, the temperature dependence of either the TFT resistance $R_{TFT}(V_{GS}, T)$ or of the charge transfer time constant $\tau_{RC}$ can be measured during detector manufacturing (on a detector-by-detector basis) and can be used in the detector adjustment. Such detector adjustment may be based on calibration data stored in table form in electronic memory, wherein numerical calibration data is associated with a particular temperature in the table, for example, as shown in FIG. 4. In one embodiment, software may also be used to program a micro-controller in the DR detector housing 312, 314, or the image processing system 34 to calculate the calibration data on the fly using a currently monitored temperature as an input to stored calibration formulas. The stored calibration formulas may be determined and stored in association with the DR detector based on the TFT measurements initially performed during manufacture of the DR detector, and as described herein below.

1. Monitor the temperature and apply a uniform adjustment of gain. In one exemplary embodiment, an average temperature dependence of either the TFT resistance or the charge transfer time constant is measured in manufacturing or is known for the transistor process. The gain (e.g., photo-sensitivity in electrons per photon) that can be measured on a pixel-by-pixel basis is calibrated at a single temperature during detector calibration (e.g., once per year). During detector operation, the gain calibration table applied to all pixels would be adjusted according to the measured temperature dependence of $R_{TFT}$ or $\tau_{RC}$. In this method embodiment, no changes in detector operation are made based on the temperature; rather, the calibration table used by the DR detector is adjusted by a uniform factor depending on the temperature.

2. Measure the temperature dependence of charge transfer time constant or of detector gain at manufacturing, modify the accessed gain table on a pixel by pixel basis: In this exemplary embodiment, the temperature dependence of either the detector gain or of charge transfer time constant $\tau_{RC}$ is measured for each pixel in the array at manufacturing and a map (e.g., or parameter list) is stored as original calibration data. In usage, the detector is re-calibrated at a single temperature (typically 25° C.). The original calibration data with the temperature dependence can then be applied to generate (calculate) a new calibration data gain table. Since the TFT resistance does not change over time, the original calibration should remain valid as a basis for the life of the detector.

3. Monitor the image lag and adjust the gain table accordingly: At lower operating DXD temperatures where charge transfer is less complete (see equation (2) herein), a sizeable fraction of the remaining charge will be read out in the next image following readout of the exposed image. In this exemplary embodiment, when the amount of image lag is monitored, then adjustments can be made to the gain table to compensate. Alternatively, the image lag can be measured on a pixel-by-pixel basis as a function of temperature at detector manufacturing and a temperature correction table generated to be applied to each gain table depending on the temperature measured in the cassette at the time of operation. In another embodiment, the image lag (e.g., image lag table) can be generated by using electrical injection prior to (or following) exposure. In this embodiment, signal charge can be electrically written to the pixel by a fill pulse in which the diode bias is reduced by a small voltage ($\Delta V_{PD}$=~0.5V) during a first readout and restored to its nominal voltage during a second readout. During the filling pulse, a signal charge with N electrons where $N=C_{PD}\Delta V_{PD}$ is written to the diode. The first frame after the fill pulse (signal frame) can be and/or the second frame after the fill pulse (lag frame) can be used to generate a correction to the gain table.

4. Monitor temperature and adjust transfer time $T_{TR}$: Since the charge transfer from the photodiode to the dataline depends only on the ratio $T_{TR}/\tau_{RC}$, if the temperature dependence of $R_{TFT}(V_{GS}, T)$ is measured, then the transfer time can be adjusted based on the measured (monitored) temperature in the cassette. In this exemplary embodiment, the micro-controller in the DR detector cassette can sense the temperature prior to image capture, and it, or the image processing 34, would access the calibration data table and accordingly may adjust the timing of the gate driver circuits 228. For example, the transfer time at 15° C. might be set to 50 µs while the transfer time at 35° C. might be set to 25 µs in the calibration data table, in order to maintain a constant ratio of $T_{TR}/\tau_{RC}$.

5. Monitor temperature and TFT adjust gate voltage: The TFT resistance, and thereby the charge transfer time constant $\tau_{RC}$, depends on the gate voltage $V_{GS}$, with a lower resistance at a higher gate voltage. In this exemplary embodiment when the gate voltage dependence of the TFT resistance is measured, then the gate voltage can be adjusted in order to maintain a constant ratio $T_{TR}/\tau_{RC}$. For example, if the micro-controller in the cassette measures a temperature of 15° C., it, or the image processing 34, would access the calibration data table and accordingly set the gate driver on-voltage to 30V while if the micro-controller measures 35° C., it would set the gate driver on-voltage to 20V to compensate for the temperature dependence of $R_{TFT}$.

6. Monitor a test circuit to sense TFT resistance or a parameter sensitive to TFT resistance and adjust either transfer time or TFT gate voltage. In this exemplary embodiment, a test circuit can be included on the detector to monitor the resistance of a test TFT prior to detector readout, then the micro-controller can modify an operating parameter such as transfer time or gate on-voltage to compensate. Such a circuit, for example, might include multiple TFT's of the same dimensions as those used as pixel switches in the array biased at a known value of $V_{DS}$. The micro-controller, or image processing 34, could set the gate voltage to a value used in detector operation and measure the current output $I_{DS}$, which would be inversely proportional to the TFT resistance. In an alternative embodiment, the micro-controller, or processor, could adjust $V_{GS}$ to achieve a target value of $I_{DS}$. The on-voltage of the gate drivers could then be set to the same voltage during detector readout. In one embodiment, the test circuit may be outside of the imaging array, while in another embodiment the test circuit may be fabricated within the imaging array (e.g., dispersed or contiguous).

7. Measure the signal charge and/or lag charge following electrical injection before capture of the radiographic image and adjust operating parameters accordingly: As described in #3 above, electrical injection can be used to write a known signal charge to each pixel and monitor the signal charge in the first image frame after electrical injection (signal frame) or the second or following image frames (lag frames). In this exemplary embodiment, the remaining charge information in lag frames can be used to adjust either the transfer time $T_{TR}$ or the gate on-voltage $V_{GS}$. In one embodiment, a process could be performed iteratively with adjustment of $T_{TR}$ or $V_{GS}$ until the signal and/or lag frames match a pre-determined stored profile.

In the first three exemplary embodiments described above, no changes to the operating parameters for a DXD are made based on the temperature. Rather, adjustment to the calibration table used for detector uniformity correction are made based on the measured temperature at the time of operation, i.e., at approximately the time of x-ray exposure and image capture. It will be apparent that many algorithms of various levels of complexity can be used to compensate the calibration data gain table for use at the actual temperature of operation. In exemplary embodiments #4 through #7 above, one or more of the operating parameters for a DXD are made based on the temperature at the time of operation or on other calibration methods (such as measurement of response to electrical injection). Other measurements or adjustments of other operating parameters or other post-processing of the images can be used that will yield similar results.

In summary, in a DR detector it is advantageous to have the capability of operating over a wide temperature range without requiring pixel-by-pixel gain calibration for each operating temperature. In order to minimize calibration time and complexity, the pixel-by-pixel gain calibration for sensitivity to X-ray exposure is performed at a single temperature (such as 25° C.). This calibration is typically performed by exposing the detector to a uniform (or known) X-ray exposure and measuring the detector output, subtracting the detector output in the absence of X-ray exposure (offset-corrected exposed image) divided by the X-ray exposure (in units such as milli-Roengten (mR) to give electrons per incident X-ray on a pixel-by pixel basis. The gain is the electrical output of the detector (in analog or digital form) divided by the X-ray input (in units such as milli-Roengten (mR)) for a standard set of X-ray exposure condition. The absolute value of the detector gain depends on parameters such as the number and wavelength of the visible photons per unit area emitted by the scintillator for the standard X-ray exposure, the optical coupling between scintillator and the array, the photo-sensing element area, the quantum efficiency vs. wavelength for the photo-sensing element in the pixel, the percentage of charge transferred from the photodiode to the readout circuit, and the conversion factor of charge to detector output signal. All of these parameters except the charge transfer efficiency (percentage of charge transferred from the photosensor to the readout circuit) are relatively independent of temperature over normal operating temperature for DR detectors. The charge transfer efficiency, however, is strongly temperature dependent and accounts for the majority of the temperature sensitivity of the gain.

The present application contemplates methods and program products on any computer readable media for accomplishing its operations. Exemplary embodiments according to the present application can be implemented using an existing computer processor, or by a special purpose computer processor incorporated for this or another purpose or by a hardwired system. Also known in the art are digital radiographic imaging detectors that utilize an array of pixels comprising an X-ray absorbing photoconductor, such as amorphous Selenium (a-Se), and a readout circuit. Since the X-rays are absorbed in the photoconductor, no separate scintillating screen is required.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

As will be appreciated by one skilled in the art, the present invention may be embodied as a system, method, or computer program product. Accordingly, an embodiment of the present invention may be in the form of an entirely hardware embodiment, an entirely software embodiment (including firmware, resident software, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or host processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

Those skilled in the art will readily recognize that the equivalent of such a computer program product may also be constructed in hardware. The computer-usable or computer-readable medium could even be paper or another suitable medium upon which executable instructions are printed, as the instructions can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport computer instructions for use by, or in connection with, an instruction execution system, apparatus, or device.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of operating a digital radiographic detector having a plurality of pixels, the method comprising:
    determining and electronically storing a gain calibration table applicable to the plurality of pixels in the detector at a first temperature;
    capturing radiographic image data using the plurality of pixels in the detector at a second temperature different from the first temperature;
    adjusting the gain calibration table based on the second temperature;
    applying the adjusted gain calibration table to the radiographic image data captured at the second temperature; and
    reading out the radiographic image data from the detector after the step of applying the adjusted gain calibration table thereto.

2. The method of claim 1, further comprising predetermining a channel resistance factor, wherein the channel resistance factor is associated with a temperature dependency of channel resistance of each of the plurality of pixels in the detector, and wherein the step of adjusting comprises uniformly adjusting the gain calibration table using the channel resistance factor.

3. The method of claim 2, wherein the channel resistance factor and the gain calibration table are stored in an electronic memory accessible by the detector.

4. The method of claim 2, further comprising determining the channel resistance factor according to a temperature formula associated with the detector.

5. The method of claim 3, further comprising determining the channel resistance factor associated with the detector at the first temperature at approximately the time of manufacture of the detector.

6. The method of claim 1, further comprising predetermining a time constant factor of the plurality of pixels in the detector and storing it in an electronic memory accessible by the detector, wherein the time constant factor is associated with a temperature dependency of a time constant of each of the plurality of pixels in the detector, and wherein the step of adjusting comprises adjusting the gain calibration table using the time constant factor.

7. The method of claim 1, further comprising predetermining an image lag factor of the plurality of pixels in the detector and storing it in an electronic memory accessible by the detector, wherein the image lag factor is associated with a temperature dependency of image lag of each of the plurality of pixels in the detector, and wherein the step of adjusting comprises adjusting the gain calibration table using the image lag factor.

8. A method of operating a digital radiographic detector, the method comprising:
    determining a pixel gate voltage associated with the detector at a first temperature;
    storing the pixel gate voltage associated with the detector at the first temperature in an electronic table accessible by the detector;
    capturing a radiographic image using the detector at a second temperature;
    determining a pixel gate voltage associated with the detector at the second temperature; and
    reading out the radiographic image data from the detector at the determined pixel gate voltage associated with the detector at the second temperature.

9. The method of claim 8, further comprising:

capturing a radiographic image using the detector at the first temperature; and reading out the radiographic image data from the detector at the determined pixel gate voltage associated with the detector at the first temperature.

10. The method of claim 8, further comprising determining the pixel gate voltage according to a temperature formula associated with the detector.

11. The method of claim 10, further comprising increasing the pixel gate voltage in response to a decreasing temperature of the detector according to the temperature formula associated with the detector.

12. The method of claim 6, further comprising using the time constant factor as a common factor for uniformly adjusting the gain calibration table.

13. The method of claim 6, further comprising determining the time constant factor according to a temperature formula associated with the detector.

14. The method of claim 6, further comprising determining the time constant factor of the plurality of pixels in the detector at the first temperature at approximately the time of manufacture of the detector.

15. The method of claim 6, further comprising using the time constant factor as a common factor for uniformly adjusting the gain calibration table.

16. The method of claim 7, further comprising determining the image lag factor according to a temperature formula associated with the detector.

17. The method of claim 7, further comprising determining the image lag factor of the plurality of pixels in the detector at the first temperature at approximately the time of manufacture of the detector.

18. The method of claim 7, further comprising using the image lag factor as a common factor for uniformly adjusting the gain calibration table.

* * * * *